United States Patent [19]

Huang et al.

[11] Patent Number: 4,920,130
[45] Date of Patent: Apr. 24, 1990

[54] QUINOLINE DERIVATIVES AND USE THEREOF AS ANTAGONISTS OF LEUKOTRIENE $D_4$

[75] Inventors: Fu-chi Huang, Gwynedd; Robert A. Galemmo, Jr., Ambler; Henry F. Campbell, North Wales, all of Pa.

[73] Assignee: Rorer Pharamceutical Corp., Fort Washington, Pa.

[21] Appl. No.: 116,597

[22] Filed: Nov. 3, 1987

[51] Int. Cl.$^5$ .................. C07D 215/12; C07D 215/14; C07D 403/02; A61K 31/47

[52] U.S. Cl. .................................. 514/311; 546/176; 546/153; 546/155; 546/156; 546/171; 546/172; 546/174; 546/175; 546/177; 546/178; 546/179; 546/180

[58] Field of Search ............... 546/176, 174, 153, 156, 546/172, 175, 177, 178, 155, 171, 179; 514/314

[56] References Cited

U.S. PATENT DOCUMENTS

| | | | |
|---|---|---|---|
| 4,282,230 | 8/1981 | Hoehn ................................. | 546/176 |
| 4,661,499 | 4/1987 | Young et al. ....................... | 514/311 |
| 4,769,461 | 9/1988 | Musser et al. ..................... | 546/152 |

FOREIGN PATENT DOCUMENTS 0206751 12/1986 European Pat. Off. ............ 546/170

Primary Examiner—David B. Springer
Attorney, Agent, or Firm—James A. Nicholson; Martin Savitzky; Imre Jim Balogh

[57] ABSTRACT

This invention relates to certain quinoline-diaryl compounds and their use as leukotriene $D_4$ antagonists for the treatment of hypersensitive disorders.

22 Claims, No Drawings

QUINOLINE DERIVATIVES AND USE THEREOF AS ANTAGONISTS OF LEUKOTRIENE D4

FIELD OF INVENTION

This invention relates to certain chemical compounds and their use as valuable pharmaceutical agents, particularly as lipoxygenase inhibitors and/or leukotriene antagonists possessing anti-inflammatory and anti-allergic properties.

SUMMARY OF THE INVENTION

This invention relates to the compounds described by the general Formula I and to therapeutic compositions comprising as active ingredient a compound of Formula I:

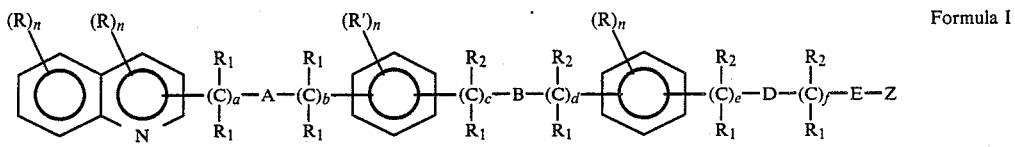

Formula I where:
A is O or S;
B is

D is O, S, NR$_1$,

or a chemical bond
E is a chemical bond or

a is 0–2;
b is 0–1;
c is 0–2;
d is 0–3;
e is 0–4;
f is 0–5;
n is 0–2;
R is independently hydrogen, alkyl, hydroxy, alkoxy, carboxy, carbalkoxy, halo, nitro, haloalkyl, cyano or acyl;
R' is independently hydrogen, alkyl, hydroxy, alkoxy, halo or haloalkyl;
R$_1$ is independently hydrogen, alkyl or aralkyl;
R$_2$ is —(CH$_2$)$_x$—X;
where x is 0–3 and X is hydrogen, alkyl, alkenyl, cycloalkyl, aryl aralkyl, hydroxy, alkoxy, aralkoxy, amino, mono-and di-alkylamino, aralkylamino, acylamino, carbamyl, carboxy, carbalkoxy, tetrazolyl or N-acylsulphamido;
vicinal R$_2$ groups together may be (CH$_2$)$_y$—where y is 1–4, thus forming a 3–6 membered ring;
geminal R$_1$ and R$_2$ groups may together form a spiro substituent, —(CH$_2$)$_z$—, where z is 2 to 5;
geminal R$_1$ or R$_1$ and R$_2$ groups may together form an alkylidenyl substituent, $$\overset{CHR_1}{\|}$$

Z is —COOR$_1$;

—CN;

$$\overset{O}{\underset{\|}{-C}}NHSO_2R_3 \text{ where } R_3 \text{ is hydrogen, alkyl, haloalkyl, phenyl or benzyl;}$$

$$\overset{O}{\underset{\|}{-C}}N(R_1)_2;$$

—OR, or tetrazolyl or substituted tetrazolyl where the substituent may be alkyl, carboxyalkyl or carbalkoxyalkyl; and pharmaceutically acceptable salts thereof.

The compounds of Formula I contain at least three aromatic rings. For the purposes of this invention these may be designated as shown in Formula II. The substitution pattern of these rings along the chain with respect to each other is as follows.

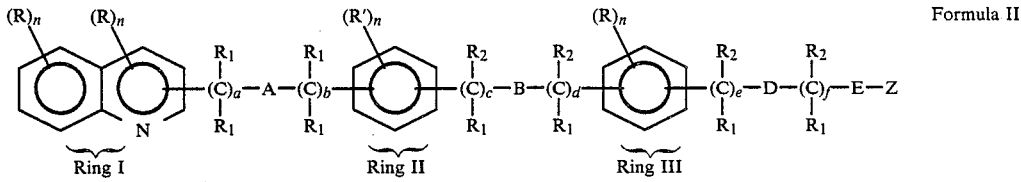

Formula II

The substitution pattern of the quinoline ring, that is Ring I, is preferably at the 2-position for extending the side chain. As this side chain progresses from the quinoline ring, the two phenyl rings, designated Ring II and Ring III may be substituted along the chain in the ortho, meta or para positions with respect to each other and Ring II may also be substituted in the ortho, meta and para positions in respect to the quinoline ring.

The preferred substitution pattern for Ring II is meta or para, that is:

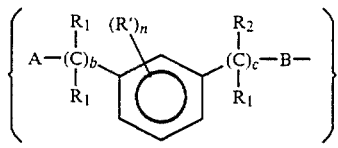

IIIa or

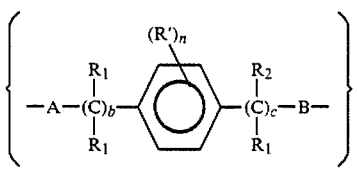

IIIb

Ring III however may be substituted equally in the ortho, metha or para positions, that is:

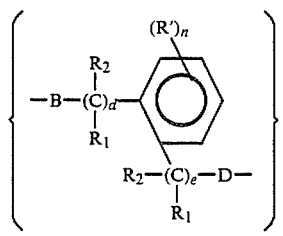

IVa

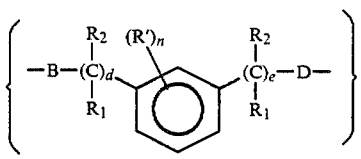

IVb or

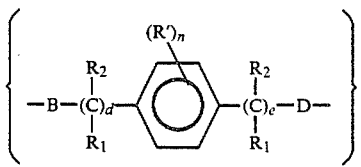

IVc

Further preferred compounds of this invention are described by Formula V below:

The more preferred compounds of Formula V are those where

Z is —COOR$_1$;

—CN; —$\overset{\overset{O}{\|}}{C}$NHSO$_2$R$_3$ or tetrazolyl.

In addition, the present invention relates to the method of using these compounds as lipoxygenase inhibitors and/or leukotriene antagonists possessing anti-inflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl-O-group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic radical derived from an organic acid by removal of its hydroxyl group. Preferred acyl groups are acetyl, propionyl, benzoyl, etc.

"Halo" means a halogen. Preferred halogens include, chloride, bromide and fluoride. The preferred haloalkyl group is trifluromethyl.

The compounds of this invention may be prepared in segments as is common to a long chain molecule. Thus it is convenient to synthesize these molecules by employing condensation reactions at the A, B and D sites of the molecule. For this reason the present compounds may be prepared by art recognized procedures from known compounds or readily preparable intermediates. Exemplary general procedures are as follows and are shown where R, R', R$_1$ and R$_2$ are all hydrogen; b, d and e are 0; a, c, and f are 1, or b, c, e and f are 0 and a and d are 1; and Z is —CN, —COOR$_1$ or tetrazolyl. Thus in order to prepare a compound of Formula I the following reactions or combinations of reactions may be employed:

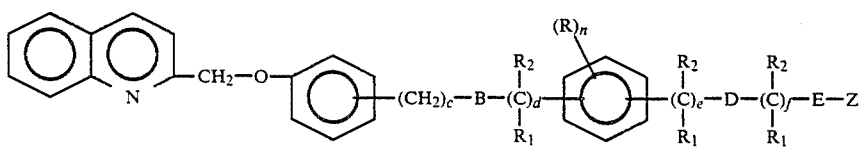

Formula V where
c+d=0–3 and R, R$_1$, R$_2$, e, f, n, B, D, E and Z are as described above.

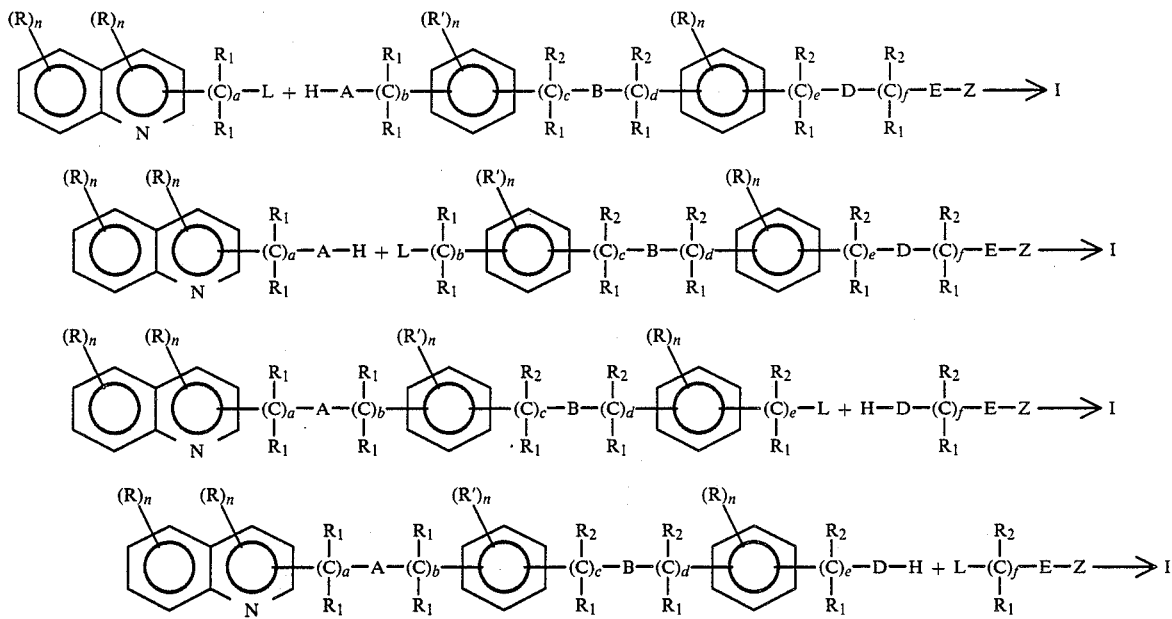

where:
R, R', $R_1$, $R_2$, a, b, c, d, e, f, n, A, B and D are as defined above; E is a chemical bond; Z is —CN, —COOR$_1$ or tetrazolyl, and L is a leaving group, such as halo, tosylate, or mesylate.

Reaction temperatures are in the range of room temperature to reflux and reaction times vary from 2 to 48 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

Wittig condensation also may take place at the B position of the molecule of Formula I as follows:

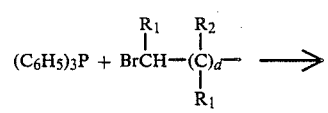

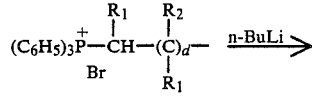

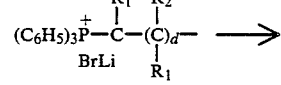

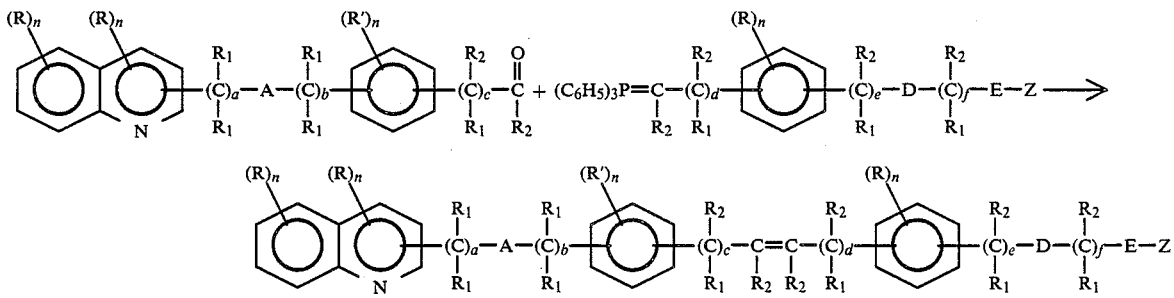

This may be carried out using normal Wittig reaction conditions. When the appropriate aldehyde or ketone is reacted with a Wittig reagent then condensation results in the formation of the double bond.

The Wittig reagent is prepared by known art recognized procedures such as reaction of triphenyl phosphine or diethylphosphone, with a substituted alkyl bromide followed by treatment with a strong organometallic or alkoxide base such as n-BuLi or NaOH results in the desired ylide.

Of course this Witting condensation may also take place when the Wittig reagent is formed on Ring II position of the molecule which is then condensed with the aldehyde from the Ring III portion.

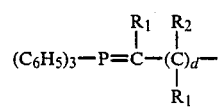

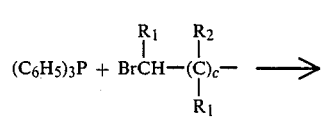

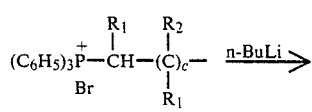

-continued

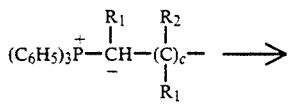

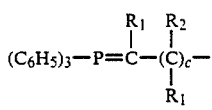

Those compounds where D and/or E are

are also prepared by reacting the appropriate aldehyde or ketone with a substituted Wittig reagent of the formula

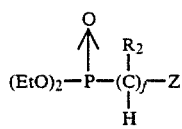

where Z is cyano or carbalkoxy.

The tetrazole may be formed from the nitrile at various stages of the synthesis by treatment with hydrazoic acid formed in situ from sodium azide and an acid.

The products of this invention may be obtained as racemic mixtures of their dextro and levorotatory isomers since at least one asymmetric carbon atom may be present. When two asymmetric carbon atoms are present the product may exist as a mixture of two disastereomers based on syn and anti configurations. These diastereomers may be separated anti configurations. These diastereomers may be separated by fractional crystallization. Each diastereomer may then be resolved into dextro and levorotatory optical isomers by conventional methods.

Resolution may best be carried out in the intermediate stage where it is convenient to combine the reacemic compound with an optically active compound by salt formation, ester formation, or amide formation to form two disasteromeric products. If an acid is added to an optically active base, then two disastereomeric salts are produced which posses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, mailic, tartaric and the like which are pharmaceutically acceptable. Basic salts for pharmaceutical use are the Na, K, Ca and Mg salts.

Various substituents on the present new compounds, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME—5505, 10 ml) according to the published procedure—(Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen–5% carbon dioxide and maintained at 37° C. The assay buffer has been made as follows: for each liter of buffer the following are added to approximately 800 ml of water distilled in glass-6.87 g NaCl, 0.4 g MgSO$_4$·7H$_2$O, and 2.0 g D-glucose. Then a solution of 0.368 g CaCl$_2$·H$_2$O in 100 ml glass-distilled water is slowly added to the buffer. Sufficient water is added to adjust the volume to 1 liter, and the solution is aerated with 95% oxygen–5% carbon dioxide. Usually 10 liters of buffer are used for an experiment with 4 tissues. After the tissues have been repeatedly washed and allowed to equilibrate in the tissue bath, they are challenged with 1M histamine. After maxium contractions have been obtained, the tissues are washed, and allowed to relax back to baseline tension. this histamine challenge procedure is repeated at least 1 to 2 more times to obtain a repeatable control response. The average response to 1M histamine for each tissue is used to normalize all other challenges.

Responses of each tissue to a predetermined concentration of leukotriene are then obtained. Usually test compounds are examined initially at 30M on resting tension of the tissues without any added agaonist or antagonist to determine if the compound has any possible intrinsic activity. The tissues are washed and the test compound is added again. Leukotriene is added after the desired preincubation time. The intrinsic activity of the compounds, and their effect on leikotriene-induced contractions are then recorded.

The results of this test for of the compounds of the this invention indicates that these compounds are considered to be useful leukotriene antagonists.

Inhibitions of ($^3$H)-LTD$_4$ Binding Membranes from Guinea Pig Lung.

A. Preparation of the Crude Receptor Fraction

This procedure was adapted from Mong et al. 1984). Male guinea pigs are sacrificed by decapitation and their lungs are quickly removed and placed in a beaker containing ice-cold homgenization buffer. The lungs are separated from connective tissue, minced with scissors, blotted dry and weighted. The tissue is then homogenized in 40 volumes (w/v) of homogenization buffer with a Polytron at a setting of 6 for 30 seconds. The homogenate is centrifuged at 1000 x g for 10 minutes (e.g. 3500 RPM, SS-34 Rotor). The supermate is filtered through two layers of cheese cloth and centrifuged at 30,000 x g for 30 minutes (e.g. 18,500 RPM SS-34 Rotor), after which the resulting pellet is resuspended in 20 volumes of assay buffer by hand homoginization using a Dounce homogenizer. The final pellet is resuspended in 10 volumes of assay buffer and kept at 4° C. until use.

B. Binding Assay

Each assay tube (16×100 mm) contains the following:
490 µl Assay Buffer
10 µl Test compound or solvent
100 µl $^3$H-LTD$_4$ (ca. 17,500 DMP)
400 µl Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to quilibrate for 4–6 hours, the readioactivity is counted with a liquid scintillation counter appropriately set for tritium.

The required control assay tubes include the following:
(a) Total Binding: No test compound is added; buffer is substituted.
(b) Non-Specific Binding: Non-labeled ligand is added at a concentration of 1M.
(c) Solvent Controls: If test compound is dissolved in a solvent, controls for both Total Binding and Non-Specific Binding containing solvent but no compounds are required.

The results of this test indicate that the compounds for this invention exhibit valuable properties which are useful in the treatment of inflammatory conditions and allergic responses.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the acitve compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, wate, ethanol, polyol (for exmple, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of seterile powders for the preparation of sterile injectable solutions, the preferred methods of preparation are vacum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physican will determine the dosage of the present therapeutic agents which will be most suitable for prophylaxis or treatment and it will vary with the form of administration and the particular compound chosen, and also, it will vary with the particular patient under treatment. He will generally wish to initiate treatement with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

The compounds of the present invention may be prepared by the following representative examples.

EXAMPLE 1

4-(2-Quinolinylmethloxy)Benzaldehyde

A solution of 0.65 g (5.4 mmol) 4-hydroxybenzaldehyde, 0.94 g (5.3 mmol) of 2-quinolinylmethylchloride, and 0.75 g (5.4 mmol) of potassium carbonate in 15 ml of DMF is heated at 60° C. overnight. The reaction mixture is poured into water. The precipitated product is collected on a filter and purified by dry column chromatography to give 4-(2-quinolinylmethyloxy)benzaldehyde.

EXAMPLE 2

When 3-hydroxybenzaldehyde of Example 1 is replaced by the compounds of Table I below, then the corresponding product is obtained.

TABLE I 2-hydroxybenzaldehyde
3-hydroxybenzaldehyde
4-hydroxybenzaldehyde
2-methyl-3-hydroxybenzaldehyde
5-methyl-3-hydroxybenzaldehyde
2-methyl-4-hydroxybenzaldehyde
3-methyl-4-hydroxybenzaldehyde
5-methoxy-3-hydroxybenzaldehyde
4-methoxy-3-hydroxybenzaldehyde
2-methoxy-3-hydroxybenzaldehyde
5-carbomethoxy-3-hydroxybenzaldehyde
3-hydroxyphenylacetaldehyde
4-hydroxyphenylacetaldehyde
3-hydroxyphenylpropionaldehyde
4-hydroxyphenylpropionaldehyde
3-hydroxyphenylisopropionaldehyde
4-hydroxyphenylisopropionaldehyde
3-hydroxyphenylbutyraldehyde
4-hydroxyphenylbutyraldehyde
3-mercaptobenzaldehyde
4-mercaptobenzaldehyde
3-hydroxyphenyl-α-methylbutyraldehyde
3-hydroxyphenyl-β-methylbutyraldehyde
4-hydroxyphenyl-α-methylbutyraldehyde
4-hydroxyphenyl-β-methylbutyraldehyde

EXAMPLE 3

When 2-quinolinylmethyl chloride of Example 1 above is replaced by the quinoline compounds of Table II below then the corresponding product is obtained.

TABLE II 2-chloromethylquinoline
2-bromomethylquinoline
2-(1-chloroethyl)quinoline
2-(2-chloroethyl)quinoline
2-bromoethylquinoline
3-chloromethylquinoline
4-chloromethylquinoline
2-(β-chloroethyl)quinoline
2-(β-chloropropyl)quinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline
2-chlorovinylquinoline
2-chloroallylquinoline
2-(1-chloro-1-methylvinyl)quinoline
2-(1-chloro-2-methylvinyl)quinoline

EXAMPLE 4

When 2-quinolinylmethylchloride of Example 1 is replaced by the compounds of Table II, Example 3 and 4-hydroxybenzaldehyde of Example 1 is replaced by the compounds of Table I, Example 2 then the corresponding product is obtained.

EXAMPLE 5

4-(4-(2-Quinolinylmethyloxy)Styryl)Benzonitrile

A suspension of 5.51 g (13.29 mmol) of (4-cyanobenzyl)-triphenylphosphonium chloride in 100 ml of dry DMF under positive nitrogen atmosphere is cooled to 0° C. and 0.50 g (20.77 mmol), of an 80% NaH in oil dispersion is added in small portions. The suspension is aged for 15 minutes at 0° C. followed by 45 minutes at room temperature to assure complete anion formation. The flask is cooled back to 0° C. and 3.5 g (13.29 mmol) of 4-(2-quinolinylmethyloxy)benzaldehyde in 20 ml of DMF is dropped in over a period of 15 minutes. The reaction is allowed to equilibrate to room temperature and stirred for 2 hours. The resultant mixture is poured into ice water and filtered. The precipitate is dissolved in $CH_2Cl_2$, dried, and concentrated in vacuo. The crude product is recrystallized from ether to give 4-(4-(2-quinolinylmethyloxy)styryl)benzonitrile. (M.P. 116° C.–112° C.)

EXAMPLE 6

When (4-cyanobenzyl)triphenylphosphonium chloride is replaced by the compounds of Table III below then the corresponding products are prepared.

TABLE VI 2-cyanobenzyl triphenylphosphonium chloride
3-cyanobenzyl triphenylphosphonium chloride
4-cyanobenzyl triphenylphosphonium chloride
3-cyano-4-methylbenzyl triphenylphosphonium chloride
4-cyano-3-methylbenzyl triphenylphosphonium chloride
3-cyanomethylbenzyl triphenylphosphonium chloride
4-cyanomethylbenzyl triphenylphosphonium chloride
3-cyanoethylbenzyl triphenylphosphonium chloride
4-cyanoethylbenzyl triphenylphosphonium chloride
3-cyanopropylbenzyl triphenylphosphonium chloride
4-cyanopropylbenzyl triphenylphosphonium chloride
3-(2-cyanopropyl)benzyl triphenylphosphonium chloride
4-(2-cyanopropyl)benzyl triphenylphosphonium chloride
3-(2-cyanobutyl)benzyl triphenylphosphonium chloride
4-(2-cyanobutyl)benzyl triphenylphosphonium chloride
3-(3-cyanobutyl)benzyl triphenylphosphonium chloride
4-(3-cyanobutyl)benzyl triphenylphosphonium chloride
3-cyanophenylethyl triphenylphosphonium chloride
4-cyanophenylethyl triphenylphosphonium chloride
3-(2-cyanopropylthio)benzyl triphenylphosphonium chloride
3-(2-cyanopropyloxy)benzyl triphenylphosphonium chloride
3-(2-cyanopropyl-N-methylamino)benzyl triphenylphosphonium chloride
3-(3-cyanopropyloxy)benzyl triphenylphosphonium chloride
4-(3-cyanopropyloxy)benzyl triphenylphosphonium chloride
4-(4-cyanobutyloxy)benzyl triphenylphosphonium chloride
4-(3-cyanobutyloxy)benzyl triphenylphosphonium chloride
3-(3-cyanobutyloxy)benzyl triphenylphosphonium chloride
3-(1-cyanovinyl)benzyl triphenylphosophonium chloride
3-(1-cyano-2-propen-3-yl)benzyl triphenylphosophonium chloride
3-(1-cyano-3-propen-3-yl)benzyl triphenylphosophonium chloride
3-(1-cyano-2-buten-4-yl)benzyl tripheny phosophonium chloride
3-(1-cyano-3-methyl-3-buten-4-yl)benzyl triphenylphosphonium chloride
3-(1-cyano-3-buten-4-yl)benzyl triphenylphosphonium chloride

EXAMPLE 7

When the Wittig reagents of Table III, Example 6 are reacted with the compounds prepared by Examples 3 and 4 following the procedure of Example 5 then the corresponding products are obtained.

EXAMPLE 8

5-(4-(4-(2-Quinolinylmethyloxy)Styryl)Phenyl)Tetrazole

A mixture of 1.15 g (3.17 mmol) of 4-(4-(2-quinolinylmethyloxy)styryl)benzonitrile 1.03 g (15.86 mmol) of sodium azide, and 1.83 (15.86 mml) of pyridine hydrochloride in 15 ml of DMF is heated at 100° C. for 48 hours and then poured into ice water. The precipitate that forms is filtered off and suspended in hot methanol and filtered to give 5-(4-(4-(2-quinolinylmethyloxy)styryl)phenyl)tetrazole. (M.P. 241° C.–243° C.)

EXAMPLE 9

When 4-(4-(2-quinolinylmethyloxy)styryl)benzonitrile of Example 8 is replaced by the nitriles of Examples 6 and 7, then the corresponding product is obtained. A representative list of compounds so prepared is shown in Table IV, below.

TABLE IV 5-(2-(3-(2-quinolinylmethyloxy)styryl)phenyl)tetrazole
5-(4-(3-(2-quinolinylmethyloxy)styryl)phenyl)tetrazole
5-(4-(4-(2-quinolinylmethyloxy)styryl)phenyl)tetrazole
5-(3-(3-(2-quinolinylmethyloxy)styryl)phenyl)tetrazole
5-(3-(4-(2-quinolinylmethyloxy)styryl)phenyl)tetrazole
5-(2-(3-(2-quinolinylmethyloxy)styryl)phenyl)tetrazole
5-(2-(4-(2-quinolinylmethyloxy)styryl)phenyl)tetrazole
5-(4-(3-(4-(2-quinolinylmethyloxy)phenyl)2-propenylphenyl)tetrazole
5-(3-(3-(3-(2-quinolinylmethyloxy)phenyl)2-propenylphenyl)tetrazole
5-(4-(3-(3-(2-quinolinylmethyloxy)phenyl)1-propenylphenyl)tetrazole
5-(4-(4-(3-(2-quinolinylmethyloxy)phenyl)3-butenylphenyl)tetrazole
5-(4-(4-(3-(2-quinolinylmethyloxy)phenyl)2-butenylphenyl)tetrazole
5-(2-(3-(2-quinolinylmethyloxy)styryl)benzyl)tetrazole
5-(4-(3-(2-quinolinylmethyloxy)styryl)benzyl)tetrazole
5-(3-(3-(2-quinolinylmethyloxy)styryl)benzyl)tetrazole
5-(2-(4-(2-quinolinylmethyloxy)styryl)benzyl)tetrazole
5-(3-(4-(2-quinolinylmethyloxy)styryl)benzyl)tetrazole
5-(4-(4-(2-quinolinylmethyloxy)styryl)benzyl)tetrazole
5-(4-(3-(2-quinolinylmethyloxy)styryl)phenethyl)-tetrazole
5-(2-(4-(2-quinolinylmethyloxy)styryl)phenethyl)-tetrazole
5-(4-(4-(2-quinolinylmethyloxy)styryl)phenethyl)-tetrazole
5-(3-(4-(2-quinolinylmethyloxy)styryl)phenethyl)-tetrazole
5-(3-(3-(2-quinolinylmethyloxy)styryl)phenethyl)-tetrazole
5-(2-(3-(2-quinolinylmethyloxy)styryl)phenethyl)-tetrazole
5-(3-(4-(3-(2-quinolinylmethyloxy)styryl)phenyl)-propyl)tetrazole
5-(3-(4-(2-quinolinylmethyloxy)styryl)phenyl)-propyl)tetrazole
5-(2-(4-(3-(2-quinolinylmethyloxy)styryl)phenyl)-propyl)tetrazole
5-(3-(4-(3-(2-quinolinylmethyloxy)styryl)phenyl)-butyl)tetrazole

EXAMPLE 10

When (4-cyanobenzyl)triphenylphosphonium chloride of Example 5 is replaced by (4-carboxybenzyl)triphenylphosphonium chloride then the product prepared is 4-(4-(2-quinolinylmethyloxy)styryl)benzoic acid.

In a similar manner the carboxylic acids of this invention may be prepared.

EXAMPLE 11

When the esters of Example 10 are used in place of the carboxylic acids then the corresponding product is obtained.

EXAMPLE 12

4-(4-(2-Quinolinylmethyloxy)Styryl)Benzoyl Chloride (0.05 mol) of 4-(4-(2-quinolinylmethyloxy)styryl)-benzoic acid in dichloromethane solution (500 ml) and chilled in an ice bath is added thionyl chloride (0.06 mol) and a few drops of dimethylformamide. Upon completion of the reaction, the clear solution is evaporated to give 4-(4-(2-quinolinylmethyloxy)styryl)benzoyl choride.

In a similar manner the acid halides of this invention may be prepared.

EXAMPLE 13

4-(4-(2-Quinolinylmethyloxy)Styryl)Benzamide

A solution of 4-(4-(2-quinolinylmethyloxy)benzyl)-benzoyl chloride (0.05 mol) in tetrahydrofuran (300 ml) is added to a concentrated ammonium hydroxide (25 ml) solution and the reaction stirred overnight. The reaction mixture is evaporated and partitioned between ethyl acetate and water. The ethyl acetate fraction is dried and evaporated to give 4-(4-(2-quinolinylmethyloxy)styryl)benzamide.

In a similar manner the amides of this invention may be prepared.

EXAMPLE 14

4-(4-(2-Quinolinylmethyloxy)Styryl)Benzoyl-N-Benzene-Sulfonamide

A reaction mixture of 0.6 g of 4-(4-(2-quinolinylmethyloxy)styryl)benzoic acid, 0.28 g of benzene-sulfonamide, 0.28 g of 4-dimethylpyridine, and 0.44 g of 1-(3-dimethylaminopropyl)-3-ethylcarbodimidehydrochloride in 50 ml of $CH_2Cl_2$ is stirred at room temperature overnight. The solvent is removed and the residue is extracted into ethyl acetate. The organic solution is washed with water, and evaporated. The product is purified by dry column chromatography to give 4-(4-(2-quinolinylmethyloxy)styryl)-benzoyl-N-benzenesulfonamide.

EXAMPLE 15

When 4-(4-(2-quinolinylmethyloxy)styryl)benzoic acid of Example 14 is replaced by the acids of this invention such as those of Example 10 then the corresponding benzene-sulfonamide compound is prepared.

When benzenesulfonamide is replaced in the above Examples by a sulfonamide of the formula $NH_2SO_2R_3$ or an amine of the formula $HN(R_1)_2$, then the corresponding product is obtained.

EXAMPLE 16

4-(3-(2-Quinolinylmethyloxy)Styryl)Benzaldehyde

A solution of diisobutyl aluminum hydride (0.01 mol) in hexane is added dropwise to a solution of methyl 4-(3-(2-quinolinylmethyloxy)styryl)benzoate (0.01 mol) in 100 ml of THF at 0° C. The reaction mixture is stirred at 0° C. got 40 minutes and then quenched with methanol and Rochelle salt. Extraction with ethyl acetate and purified by column chromatography gives 4-(3-(2-quinolinylmethyloxy)styryl)-benzaldehyde.

EXAMPLE 17

When the esters of Example 11 is used in place of methyl 4-(3-(2-quinolinylmethyloxy)styryl)benzoate in Example 16 then the corresponding aldehyde is obtained.

EXAMPLE 18

4-(3-(2-Quinolinylmethyloxy)Styryl)Cinnamylnitrile

Sodium hydride (60% oil dispersion, 1.2 g) and diethylcyanomethylphosphonate (5 ml) are combined and stirred in THF (50 ml) for 5 minutes. This is then added to a THF solution of 4-(3-(2-quinolinylmethyloxy)-styryl)benzaldehyde (9.5 g). The reaction mixture is stirred for an additional 30 minutes and poured into ice water. The crude product is filtered and chromatogramed through a silica gel dry column using chloroform as the eluant to give 4-(3-(2-quinolinylmethyloxy)-styryl)cinnamylnitrile.

EXAMPLE 19

When 4-(3-(2-quinolinylmethyloxy)styryl)benzaldehyde of Example 18 is replaced by the compounds of Example 17, the corresponding product is prepared.

When diethylcyanomethylphosphonate in the above Example is replaced by diethylcyanoethylphosphate, diethylcyanopropylphospate or diethylcyanoisopropylphosphate then the corresponding products are obtained.

EXAMPLE 20

5-(4-(3-(2-Quinolinylmethlyoxy)Styryl)Styryltetrazole Hydrochloride

A mixture of 4-(3-(2-quinolinylmethyl)benzyloxy)-cinnamylnitrile (0.03 mol), anhydrous aluminum chloride (0.03 mol) and sodium azide (0.09 mol) in THF (30 ml) is stirred and refluxed for 18 hours. Hydrochloric acid (18% HCl 15 ml) is added and thereafter the reaction mixture is poured into ice water. The precipitate is collected and then recrystalized from methanol-ethyl acetate to obtain pure 5-(4-(3-(2-quinolinylmethyloxy)-styryl)styryl)-tetrazole hydrochloride.

The free base is obtained by treatment of the salt with one equivalent of sodium hydroxide solution followed by removal of sodium chloride and water.

EXAMPLE 21

When 4-(3-(2-quinolinylmethyloxy)styryl)cinnamylnitrile of Example 20 is replaced by the compounds formed in Example 19, then the corresponding product is prepared. Representative compounds prepared by this invention are described in Table V.

TABLE V 5-(3-(3-(2-quinolinylmethyloxy)styryl)styryl)tetrazole
5-(4-(3-(2-quinolinylmethyloxy)phenyl)2-propenyl)-styryl)tetrazole
5-(3-(4-(2-quinolinylmethyloxy)styryl)styryl)-tetrazole
5-(4-(4-(4-(2-quinolinylmethyloxy)phenyl)3-butenyl)-styryl)tetrazole
5-(4-(3-(2-quinolinylmethyloxy)4-methylstyryl)-styryl)tetrazole
5-(4-(3-(2-quinolinylmethyloxy)styryl)3-methyl-styryl)tetrazole
5-(3-(3-(2-quinolinylmethylthio)styryl)styryl)-tetrazole
5-(-3-(4-(2-quinolinylmethylthio)phenyl)-2-propenyl)styryl)tetrazole
5-(3-(3-(4-(2-quinolinylmethyloxy)phenyl)-3-pentenyl)-

TABLE V-continued styryl)tetrazole
5-(3-(4-(3-(2-quinolinylmethyloxy)styryl)phenoxy)-2-propen-1-yl)tetrazole

EXAMPLE 22

Ethyl 5-(4-(4-(2-Quinolinylmethyloxy)Styryl)Phenyl)-Tetrazol-3-yl)Acetate

To a solution of 0.2 g sodium in 30 ml ethanol is first added 1 g of 5-(4-(4-(2-quinolinylmethyloxy)styryl)-phenyl)-tetrazole and then after 30 minutes 0.6 g of ethylbromacetate and stirring is continued at 80° C. for 16 hours. The solvent is then removed, diluted with water, filtered, washed with ether and dried to give ethyl 5-(4-(4-(2-quinolinylmethyloxy)styryl)phenyl)tetrazol-3-yl)-acetate.

When ethylbromoacetate in the above procedure is replaced with N,N-diethyl-α-bromoacetamide, N,N-diethylaminoethyl bromide or N-acetylaminoethyl bromide or N-acetyl-α-bromoacetamide, then the corresponding products are obtained.

EXAMPLE 23

5-(4-(4-(2-Quinolinylmethyloxy)Styryl)Phenyl)Tetrazol-3-yl) Acetic Acid

A mixture of 1 g of ethyl [5-(3-(4-(2-quinolinylmethyloxy)styryl)phenyl)tetrazol-3-yl]acetate in 5 ml ethanol and 40 ml of 1N NaOH is stirred at 70° C. for 4 hours. This is cooled, diluted with water, acidified with acetic acid, filtered, washed with water, and then ethyl acetate to give 5-(4-(4-(2-quinolinylmethyloxy)styryl)-phenyl)tetrazol-3-yl acetic acid.

In a similar manner the substituted tetrazoles of this invention may be prepared.

EXAMPLE 24

4-(4-(2-Quinolinylmethylsulfinyl)Styryl)Benzoic Acid 4-(4-(2-Quinolinylmethylsulfonyl)Styryl)Benzoic Acid A. 4-(4-(2-quinolinylmethylthio)styryl)benzoic acid (4 mmol) in dichloroethene (50 ml) is stirred with m-chloroperbenzoic acid (4 mmol) and solid potassium hydrogen carbonate (1.0 g). The reaction is assayed by TLC and upon consumption of the starting thio compound, the mixture is filtered, washed with dilute aqueous sodium bisulfite, dried and evaporated to give 4-(4-(2-quinolinylmethylsulfinyl)styryl)benzoic acid.

B. To 3 mmol of the sulfinyl compound from Step A in acetic acid (40 mmol) is added 30% hydrogen peroxide (2 ml). The mixture is stirred at ambient temperature and assayed by TLC. Upon disappearance of the sulfinyl starting compound, the reaction mixture is diluted with dichloromethane, washed with dilute aqueous sodium bisulfite and water, dried and evaporated to give 4-(4-(2-quinolinylmethylsulfonyl)-styryl)benzoic acid.

In a similar manner the sulfinyl and sulfonyl compounds of this invention may be prepared.

EXAMPLE 25

4-(4-(2-Quinolinylmethyloxy)Styryl)Phenol

A suspension of (13.29 mmol) of 4-(2-quinolinylmethyloxy)benzyl triphenylphosphonium chloride in 100 ml of dry DMF under positive nitrogen atmosphere is cooled to 0° C. and 0.50 g (20.77 mmol), of an 80% NaH in oil dispersion is added in small portions. The suspension is aged for 15 minutes at 0° C. followed by 45 minutes at room temperature to assure complete anion formation. The flask is cooled back to 0° C. and (13.29 mmol) of 4-hydroxybenzaldehyde in 20 ml of DMF is dropped in over a period of 15 minutes. The reaction is allowed to equilibrate to room temperature and stirred for 2 hours. The resultant mixture is poured into ice water and filtered. The precipitate is dissolved in CH$_2$Cl$_2$, dried, and concentrated in vacuo. The crude product is recrystallized from ether to give 4-(4-(2-quinolinylmethyloxy)styryl)phenol.

EXAMPLE 26

When 4-(2-quinolinylmethyloxy)benzyl triphenylphosphonium chloride of Example 25 is replaced by the Wittig reagents formed from the compounds of Table II, Example 3 and 4-hydroxybenzaldehyde of Example 25 is replaced by the aldehydes of Table I, Example 2, then the corresponding product is obtained.

EXAMPLE 27

5-(3-Chloropropyl)Tetrazole

A mixture of 4-chlorobutyronitrile, (0.05 mol) sodium azide (0.20 mol) and anhydrous aluminum chloride (0.05 mol) in 100 ml of dry tetrahydrofuran is refluxed for 24 hours. After cooling to ambient temperature the reaction is acidified with 75 ml of 15% hydrochloric acid while the hydrazoic acid generated is removed by means of an aspirator. The organic and aqueous layers are then separated and the aqueous layer extracted with ethylacetate. The combined organic extracts are dried (magnesium sulfate) and evaporated to give 5-(3-chloropropyl)tetrazole which is used directly in the next step.

EXAMPLE 28

When 4-chlorobutyronitrile of Example 41 above is replaced by the nitriles of Table VI below then the corresponding tetrazole product is obtained.

TABLE VI chloroacetonitrile
bromoacetonitrile
3-chloropropionitrile
4-chlorobutyronitrile
5-chloropentanonitrile
6-chlorohexanonitrile
2-chlorporopionitrile
2-methyl-3-chloropropionitrile
2-chlorobutyronitrile
3-chlorobutyronitrile
4-methyl-5-chloropentanonitrile
2-methyl-3-chloropropionitrile
3-benzyl-4-chlorobutyronitrile
3-carbethoxymethyl-4-chlorobutyronitrile
3-methoxymethyl-4-chlorobutyronitrile
2,3-diemthyl-4-chloropentanonitrile
3,3-dimethyl-4-chloropentanonitrile
sprio-(3,3-cyclopropane)-4-chlorobutyronitrile
1-chloromethyl-2-cyanomethylcyclobutane
1-chloromethyl-2-cyanomethylcyclohexane
3-cyclopropylmethyl-4-chlorobutyronitrile
3-dimethylaminomethyl-4-chlorobutyronitrile
3-methylene-4-chlorobutyronitrile
3-propylidene-4-chlorobutyronitrile

EXAMPLE 29

5-(3-(4-(4-(2-Quinolinylmethyloxy)Styryl)Phenoxy)-Propyl)-Tetrazole

A mixture of (0.014 mol) 4-(4-(2-quinolinylmethyloxy)-styryl)phenol (0.14 mol) 5-(3-chloropropyl)tetrazole and 2 g (0.036 mol) KOH in 5 ml water and 50 ml ethanol is heated over a steam bath for a period of 3 hours. Reaction mixture is concentrated to dryness and slurried into water and extracted with methylene chloride. The methylene chloride extract is washed with water, dried over $MgSO_4$ and concentrated under reduced pressure to obtain solid which is passed through a silica gel column using hexane/ethyl acetate as eluent. Evaporation of eluent gives 5-(3-(4-(4-(2-quinolinylmethyloxy)styryl)phenoxy)propyl)-tetrazole.

EXAMPLE 30

When 4-(4-(2-quinolinylmethyloxy)styryl)phenol of Example 29 is replaced by the compounds prepared by Example 26 and 5-(3-chloropropyl)tetrazole is replaced by the compounds prepared by Example 28, then the corresponding product is obtained. A representative list of compounds so prepared is shown below in Table VII.

TABLE VII

| |
|---|
| 5-(4-(3-(3-(2-quinolinylmethyloxy)styryl)phenoxy)-butyl)tetrazole |
| 5-(3-(3-(4-(2-quinolinylmethyloxy)phenylallyl)-phenoxy)butyl)tetrazole |
| 5-(4-(4-(4-(2-quinolinylmethyloxy)phenyl)2-butenyl)-phenoxy)butyl)tetrazole |
| 5-(2-(3-(4-(2-quinolinylmethyloxy)styryl)phenoxy)-butyl)tetrazole |
| 5-(4-(3-(3-(2-quinolinylmethyloxy)styryl)phenoxy)-butyl)tetrazole |
| 5-(2-(3-(4-(2-quinolinylmethyloxy)styryl)phenoxy)-propyl)tetrazole |
| 5-(2-(3-(3-(4-(2-quinolinylmethyloxy)phenyl)2-propenyl)phenoxy)ethyl)tetrazole |
| 5-(4-(2-(4-(2-quinolinylmethyloxy)styryl)phenoxy)-butyl)tetrazole |
| 5-(3-(4-(2-quinolinylmethyloxy)styryl)phenoxy-methyl)tetrazole |
| 5-(2-(4-(2-quinolinylmethyloxy)styryl)phenoxy-methyl)tetrazole |
| 5-(4-(4-(2-quinolinylmethyloxy)styryl)phenoxy-methyl)tetrazole |
| 5-(2-(3-(2-quinolinylmethyloxy)styryl)phenoxy-methyl)tetrazole |
| 5-(3-(3-(2-quinolinylmethyloxy)styryl)phenoxy-methyl)tetrazole |
| 5-(4-(3-(2-quinolinylmethyloxy)styryl)phenoxy-methyl)tetrazole |

We claim:

1. A compound of the formula

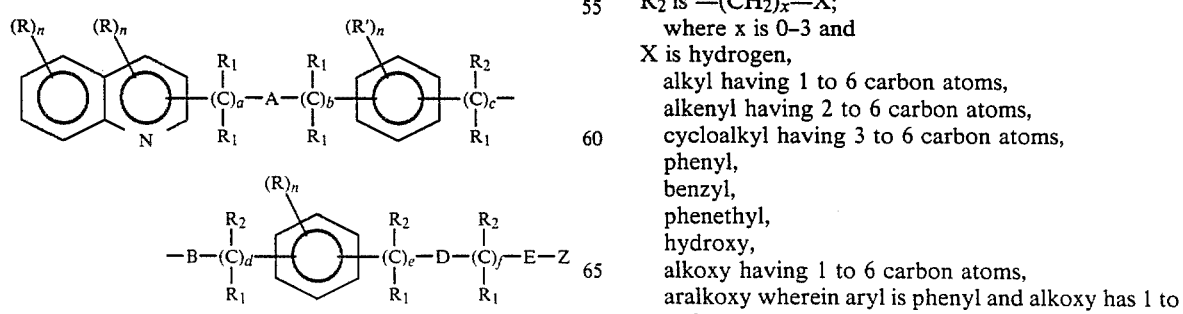

where:

A is O or S;

B is

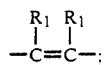

D is O, S, $NR_1$,

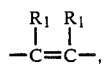

or a chemical bond;

E is a chemical bond or

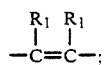

a is 0-2;
b is 0-1;
c is 0-2;
d is 0-3;
e is 0-4;
f is 0-5;
n is 0-2;
R is independently
  hydrogen,
  alkyl having 1 to 6 carbon atoms,
  hydroxy,
  alkoxy having 1 to 6 carbon atoms,
  carboxy,
  carbalkoxy wherein alkoxy has 1 to 6 carbon atoms,
  halo,
  nitro,
  trifluoromethyl,
  cyano,
  acetyl,
  propionyl or
  benzoyl;
R' is independently
  hydrogen,
  alkyl having 1 to 6 carbon atoms,
  hydroxy,
  alkoxy having 1 to 6 carbon atoms,
  halo or
  trifluoromethyl;
$R_1$ is independently
  hydrogen,
  alkyl having 1 to 6 carbon atoms,
  benzyl or
  phenethyl;
$R_2$ is $-(CH_2)_x-X$;
  where x is 0-3 and
X is hydrogen,
  alkyl having 1 to 6 carbon atoms,
  alkenyl having 2 to 6 carbon atoms,
  cycloalkyl having 3 to 6 carbon atoms,
  phenyl,
  benzyl,
  phenethyl,
  hydroxy,
  alkoxy having 1 to 6 carbon atoms,
  aralkoxy wherein aryl is phenyl and alkoxy has 1 to 6 carbon atoms,
  amino, mono- and di-alkylamino having 1 to 6 carbon atoms,
benzylamino,
phenethylamino,
acetylamino,
propionylamino,
benzoylamino,
carbamyl,
carboxy,
carbalkoxy wherein alkoxy has 1 to 6 carbon atoms,
tetrazolyl,
N-acetylsulfonamido,
N-propionylsulfonamido or
N-benzoylsulfonamido;
vicinal $R_2$ groups together may be $(CH_2)_y$— where y is 1-4, thus forming a 3-6 membered ring;
geminal $R_1$ and $R_2$ groups may together form a spiro substituent, —$(CH_2)_z$—, where z is 2 to 5;
geminal $R_1$ or $R_1$ and $R_2$ groups may together form an alkylidenyl substituent,

Z is —$COOR_1$;
—CN;

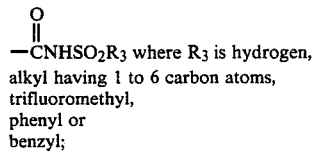

—$CNHSO_2R_3$ where $R_3$ is hydrogen,
alkyl having 1 to 6 carbon atoms,
trifluoromethyl,
phenyl or
benzyl;

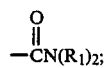

—$OR_1$ or
tetrazolyl or substituted tetrazolyl where the substituent may be alkyl having 1 to 6 carbon atoms,
carboxyalkyl wherein alkyl has 1 to 6 carbon atoms, or
carbalkoxyalkyl wherein alkoxy has 1 to 6 carbon atoms and alkyl has 1 to 6 carbon atoms; and
pharmaceutically acceptable salts thereof.

2. A compound according to claim 1 where:
A is O or S;
n is 0-1;
a+b is 1;
c+d is 0-3;
e+f is 0-5;
R and R' are hydrogen,
alkyl having 1 to 6 carbon atoms or
alkoxy having 1 to 6 carbon atoms;
$R_1$ is hydrogen or
alkyl having 1 to 6 carbon atoms;
$R_2$ is —$(CH_2)_x$—X where x is 0-3 and X is hydrogen or alkyl having 1 to 6 carbon atoms; and
Z is

—$COOR_1$;
—CN;

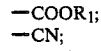
—$CNHSO_2R_3$;

—$CN(R_1)_2$ or
tetrazolyl.

3. A compound according to claim 2 where:
A is O;
n is 0;
R and R' are hydrogen, methyl or methoxy;
$R_1$ is hydrogen or methyl;
$R_2$ is —$(CH_2)_x$ where x is 0-3 and X is hydrogen; and
Z is
—$COOR_1$;
—CN or
—tetrazolyl.

4. A compund according to claim 3 where:
a is 1;
b is 0; and
c+d is 0.

5. A compound according to claim 3 where:
a is 1;
b is 0; and
c+d is 1.

6. A compound according to claim 3 where:
a is 1;
b is 0; and
c+d is 2.

7. A compound according to claim 4 where:
D is O;
e+f is 2-4; and
Z is tetrazoyl.

8. A compound according to claim 4 where:
D is a chemcial bond;
e+f is 0-6; and
Z is tetrazolyl.

9. A compound according to claim 7 which is:
5-(3-(3-(3-(2-quinolinylmethyloxy)styryl)phenoxy)propyl)tetrazole.

10. A compound according to claim 7 which is:
5-(3-(4-(3-(2-quinolinylmethyloxy)styryl)phenoxy)propyl)tetrazole.

11. A compound according to claim 7 which is:
5-(3-(3-(4-(2-quinolinylmethyloxy)styryl)phenoxy)propyl)tetrazole.

12. A compound according to claim 7 which is:
5-(3-(4-(4-(2-quinolinylmethyloxy)styryl)phenoxy)propyl)tetrazole.

13. A compound according to claim 8 which is:
5-(3-(3-(3-(2-quinolinylmethyloxy)styryl)phenyl)propyl)tetrazole.

14. A compound according to claim 8 which is:
5-(4-(3-(3-(2-quinolinylmethyloxy)styryl)phenyl)butyl)tetrazole.

15. A compound according to claim 8 which is:
5-(4-(4-(3-(2-quinolinylmethyloxy)styryl)phenyl)butyl)tetrazole.

16. A compound according to claim 8 which is:
5-(3-methyl-4-(4-(3-(2-quinolinylmethyloxy)styryl)phenyl)butyl)tetrazole.

17. A compound according to claim 8 which is:
5-(4-(3-(3-(2-quinolinylmethyloxy)styryl)phenyl)butyl)tetrazole.

18. A compound according to claim 8 which is:
5-(3-methyl-4-(3-(3-(2-quinolinylmethyloxy)styryl)phenyl)butyl)tetrazole.

19. A compound according to claim 8 which is:

5-(4-(4-(4-(2-quinolinylmethyloxy)styryl)phenyl)-butyl)tetrazole.

20. A compound according to claim 8 which is:
5-(3-methyl-4-(4-(2-quinolinylmethyloxy)styryl)-phenyl)butyl)tetrazole.

21. A method for the treatment of hypersensitive ailments in a patient requiring such treatment which comprises administering to such patient an effective amount of a compound of the formula according to claim 1.

22. A pharmaceutical composition for the treatment of hypersensitive ailments in a patient requiring such treatment comprising an effective amount of a compound according to claim 1 in admixture with a pharmaceutical carrier.

* * * * *